US00PP13100P2

(12) United States Plant Patent
Bennett et al.

(10) Patent No.: US PP13,100 P2
(45) Date of Patent: Oct. 22, 2002

(54) SEASHORE PASPALUM 'SGX-6'

(76) Inventors: Stewart T. Bennett, 14261 Clubhouse Dr., Bekerlia, FL (US) 33922; Michael DePew, 835 Herricksville Rd., Tekonsha, MI (US) 49092

( * ) Notice: Subject to any disclaimer, the term of this patent is extended or adjusted under 35 U.S.C. 154(b) by 0 days.

(21) Appl. No.: 09/502,904

(22) Filed: Feb. 11, 2000

(51) Int. Cl.[7] ..... A01H 5/00

(52) U.S. Cl. ..... Plt./388

(58) Field of Search ..... Plt./388

(56) References Cited

PUBLICATIONS

U.S. patent application Ser. No. 09/643,598, DePew et al., filed Aug. 22, 2000.

U.S. patent application Ser. No. 09/643,286, DePew et al., filed Aug. 22, 2000.

U.S. patent application Ser. No. 09/759,481, DePew et al., filed Jan. 12, 2001.

*Primary Examiner*—Bruce R. Campell
*Assistant Examiner*—Annette Para
(74) *Attorney, Agent, or Firm*—Laura G. Barrow

(57) ABSTRACT

A new and distinct cultivar of seashore paspalum grass is disclosed. The 'SGX-6' variety is characterized by its fine texture when closely mown and its superior tolerance to salt, drought, and soil hypoxic conditions.

5 Drawing Sheets

SUMMARY OF THE INVENTION

The present invention relates to a new cultivar of seashore paspalum (*Paspalum vaginatum* Swartz) that is particularly suited as a turf grass for recreational fields and golf courses. The new cultivar of the present invention is herein referred to by its cultivar name 'SGX-6.'

The 'SGX-6' cultivar is a low growing halophytic grass spreading by rhizomes and stolons. The grass is particularly well suited for use on golf courses for tees and fairways mowed to 5/8 inch and for putting greens mowed to 3/16 inch. It also suitable for lawns and athletic fields or any other area where a fine textured, close mown and low growing turf with superior salt tolerance is desired.

DETAILED DESCRIPTION OF THE VARIETY

The following is a detailed description of the new grass variety based upon observation of the grass grown in field plots and under live golf conditions on a local golf course.

Figure 1:
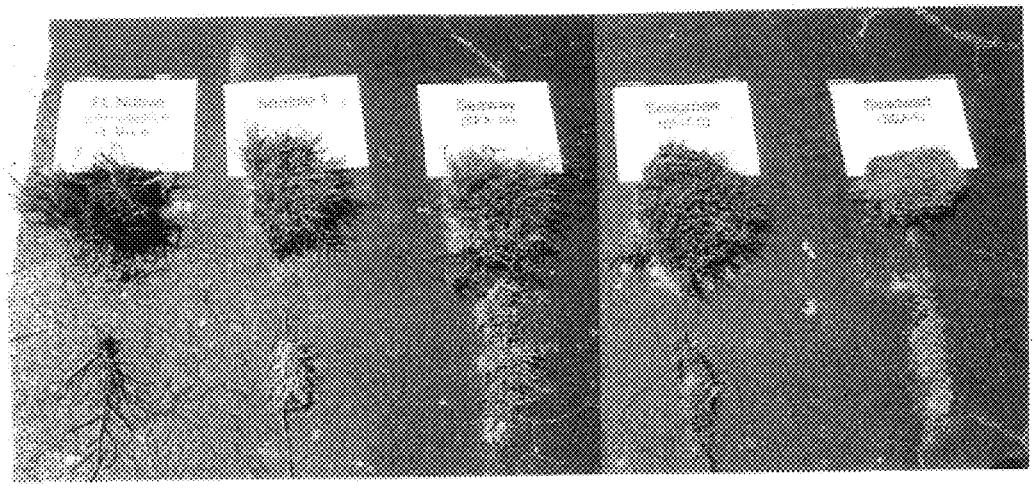
FIG. 1 is shows a comparison of the inventive cultivar with a Florida native (natural) ecotype and four improved turf-type varieties. These varieties, from left to right, are Florida native type, 'SeaIsle 1' (University of Georgia release), Applicants' variety 'SFX-14' (Ser. No. 09/502,903), Appliants' variety 'SGX-6', and Applicant's seashore paspalum variety named 'SDX-1' (Ser. No. 09/759,481).

FIG. 1 represents plugs of Seashore paspalum sod for one Florida native ecotype and four other seashore pasplum varieties, including Applicants' present 'SDX-6' variety. Beneath each sod plug is a stolon from each variety collected where grass was encroaching on unvegetated ground adjacent to the established grassed areas. The four turf-type sod samples represent the stand 120 days following sprigging, maintained with slightly brackish water (2,000–5,000 ppm) grown in a 90:10 sand-peat zone blend. The appearance of the three turf-type grass varieties of 'SeaIsle 1', 'SFX-14', and 'SGX-6' represent a maintenance regime with a mow height of 2.5 inches (6.35 mm) followed by a period of two weeks without mowing prior to collection and photographing. The 'SDX-1' variety was unmown.

Figure 2:
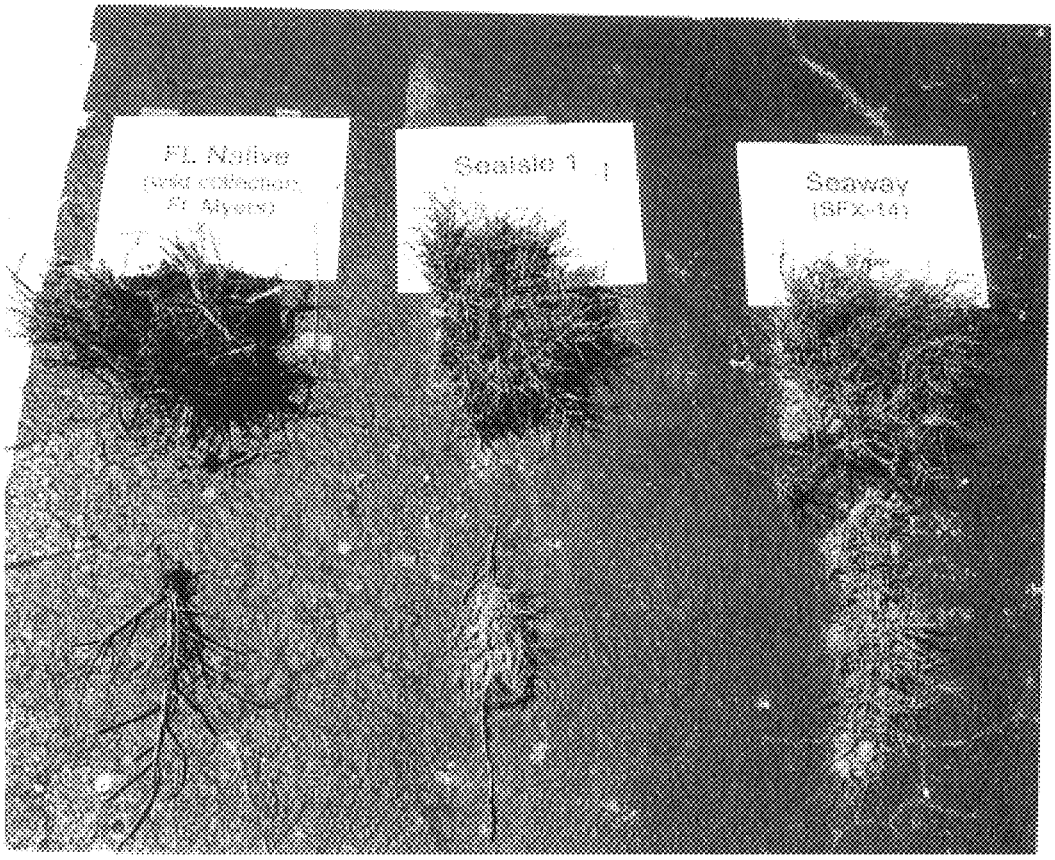
FIG. 2 shows a closer view of the turf samples shown in FIG. 1.

FIG. 2 shows differences in the amount and vigor of growth exhibited in the 'SDX-6' variety from two weeks following the last mowing.

Figure 3:
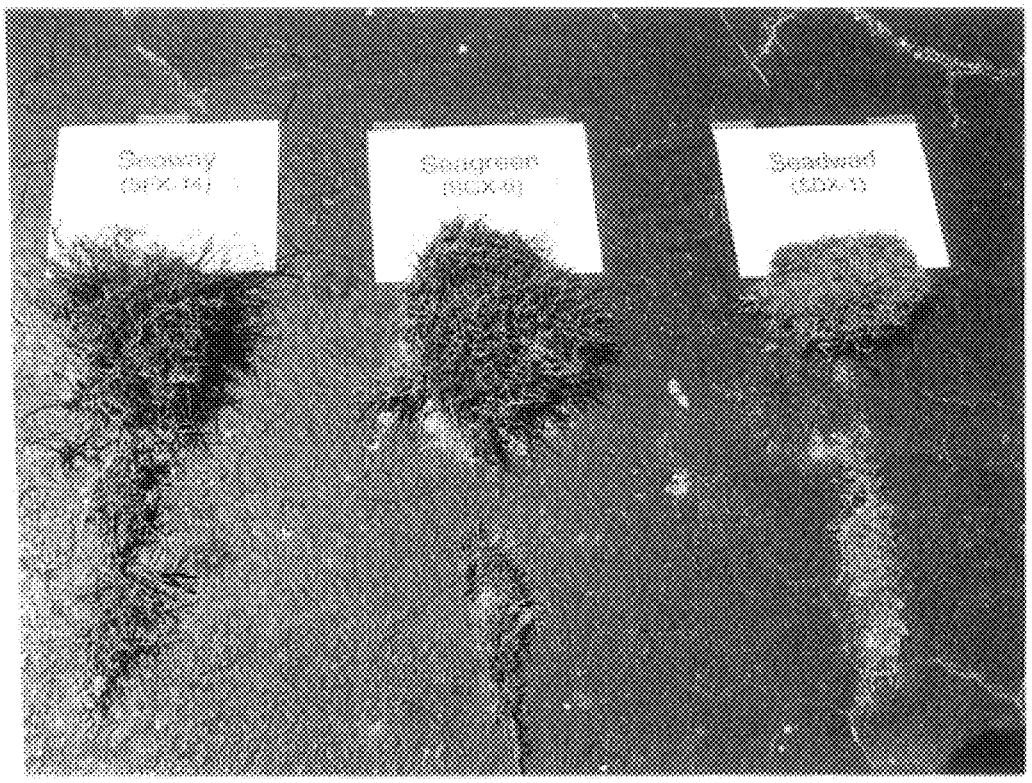
FIG. 3 is a closer view of the turf samples shown in FIG. 1.

FIG. 3 shows a closer view of the turf grasses shown in FIGS. 1–2. Under same growth and maintenance conditions, the difference is clearly noted between the 'SFX-14' variety and the Applicants' 'SDX-6' variety in that the 'SDX-6' variety is shorter in overall height, forming a denser and tighter sod, and has shorter stolon growth and denser development of shoots along the stolon and the secondary branches of the stolon.

Figure 4:
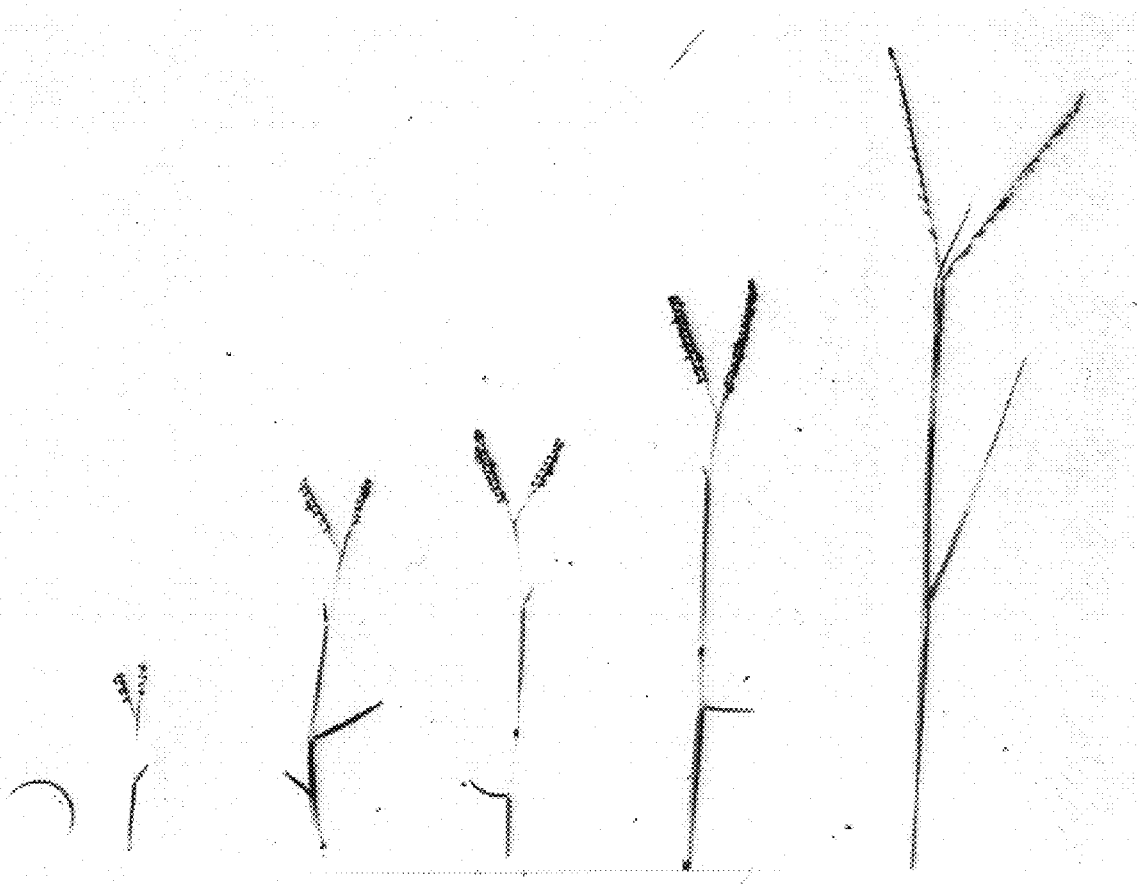
FIG. 4 shows seedheads form various seashore paspalum varieties. These varieties, from left to right, are Florida native type, 'SeaIsle 1' (University of Georgia release), Applicants' variety 'SFX-14', Appliants' variety 'SGX-6', and Applicant's seashore paspalum variety named 'SDX-1'.
Figure 5:
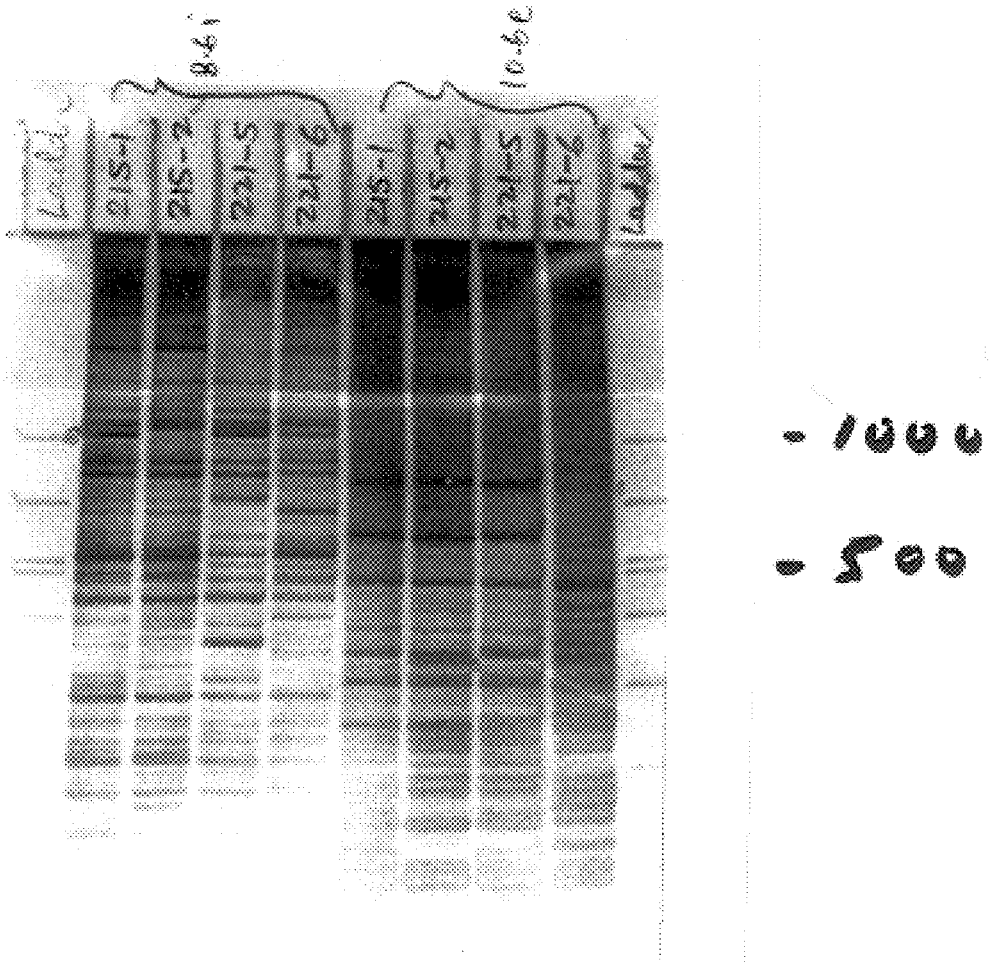
FIG. 5 shows DNA amplification profiles of 'SFX-14' variety, 'Adalayd,' Applicants' 'SGX-6' variety, and native seashore paspalum.

FIG. 4 shows typical seedheads for each turf-type variety grown under the same conditions, notwithstanding the fact that the size and appearance of the seedheads vary somewhat within a variety.

Asexual Reproduction

The 'SGX-6' grass was developed by the applicants on Pine Island, Fla. in a saline environment. Florida native ecotypes were collected from salt marsh locations and commingled in mixed populations with an 'Adalayd' cultivar of seashore paspalum. These mixed population strains were maintained under close mown conditions with high traffic stress and saline irrigation. During periods of seed head production, the grasses were allowed to flower and produce seed. The seeds were allowed to drop and germinate naturally. With the resumption of close-mown conditions and high traffic stress, selections of this grass were isolated from the mixed colonies and asexually propagated. Trial areas of the asexually-propagated grass (i.e. 'SGX-6' cultivar) were established and maintained under live golf conditions at Alden Pines Country Club in Bokeelia, Fla., a salt water irrigated golf course, since 1994. The age of the plant observed for botanical description was approximately 180 days old. All subsequent asexual reproductions of the 'SGX-6' grass observed to date have been true to the original variety and remain true to type when asexually reproduced. This grass selection, while similar in appearance and form to applicants' 'SFX-14' cultivar, is particularly well adapted to close mown and high traffic putting green applications. This grass has been asexually propagated by the applicants as sprigs, plugs, and sod.

Botanical Description

The 'SGX-6' cultivar is a perennial grass. The grass stems have overlapping sheath margins and arise from an extensive system of long, straw colored, slender rhizomes and/or purple-tinged stolons. The grass blades are glabrous and folded, forming a V-shape. The grass blades have an olive green color, Munsell color designation 7.5 GY 4/4 (abaxial side) and 7.5GY 5/4 (adaxial side). The blade length is generally 1.75–2.25 cm (unmown). The blades have a typical width of from 1.4 to 1.9 mm, varying with the level of salinity, and taper to an involute apex. Leaf-blade venation of the variety is parallel without cross veins. Veins obscure with a prominent mid-vein. Leaf margins are smooth, and leaf auricles are absent. Upon flowering, the culms are about 1.5–3 cm tall with inflorescence forming paired branches (racemes) at the culm apex. The racemes are about 0.8 to 2.25 cm in length, each having a broad, triangular rachis bearing two rows of spikelets (one floret per spikelet). Ligules have an eciliate membrane. The collar does not have an external ligule.

Upon flowering, culms mostly 1.5–3 cm tall with terminal inflorescence subtended by an unspecialized leaf-sheath. The inflorescence of the variety bears well-developed spikelets at emergence forming paired branches (racemes) at the culm apex about 0.8–2.25 cm in length. Racemes have a broad triangular rachis with spikelets (one floret per spikelet) borne in two rows. The variety has angular, narrowly winged rhachis, which is tough, persistent, 1–2 mm wide, and terminates in a spikelet. Spikelet packing is regular, two-rowed, abaxial, contiguous, and has subequal internodes. Florets (seed) are ovate and 0.5–0.75 mm in diameter. Glumes, palea, and lemma are awnless, glabrous, green, and have an acute apex.

Leaf blade width and length of the 'SGX-6' cultivar are affected by both salinity level and by the length of sunlight exposure. In the winter months, shorter, narrower leaf blades are produced compared to longer, wider leaf blades produced during the summer. Likewise, as salinity levels increase, shorter, narrower, and somewhat more erect leaf blades are produced, compared to longer, wider blades produced upon irrigation with a fresh water or low salinity system.

General Observations

The 'SGX-6' cultivar has shown to be particularly well suited for use on golf putting green surfaces due to its high shoot density and fine texture produced under close mown conditions and saline irrigation. This grass has been tested under long term saline irrigation up to 15,000 ppm and has also survived seawater flooding from tropical storms and hurricanes. The applicants have also utilized periodic seawater and brine water (45,000 ppm) drenches on putting green surfaces for pest and weed control with no apparent damage to the grass. Direct applications of table salt or sea salt have also been employed for weed control, although temporary burning of the grass leaf tips have been observed with heavy salt applications.

Compared to 'Adalayd' and 'Excalibre' seashore paspalum cultivars (sold and produced by others) and which are utilized for similar purposes, the 'SGX-6' cultivar has foremost greater salinity tolerance and, under saline conditions, improved density, finer texture, greater sod strength, increased rooting, and improved color (the winter color is more true (i.e. remains green) compared to the 'Adalayd', which gets more of a blue tint in the winter months). Compared to other fine textured grass species for similar uses (notably common and hybrid bermudagrass), this grass has adaptations for moderate to heavy shade tolerance and enhanced temperature tolerance, retaining color at lower temperatures than bermudagrasses. This grass has enhanced qualities for drought tolerance and can be grown in sandy soils as well as in heavy textured waterlogged soils. Also, this grass has a better tolerance to soil hypoxic conditions than the 'Adalayd' grass.

Compared to the SGX-6 variety, the Florida native seashore paspalum ecotypes utilized in the inventors' program have leaf blades that are coarser (3–8 mm wide), longer (3.5–15 cm long), and have a much higher overall shoot height (often exceeding 50 cm unmown), with a culm height often exceeding 60 cm. Raceme branches of the Florida native seashore paspalum ecotypes are much longer than those of the SGX-6 variety, typically 4–8 cm in length. The Florida native seashore paspalum ecotypes also do not exhibit significant rhizome development (being primarily stoloniferous), do not form a dense, thick stand of grass suitable for most turf grass applications, nor do they form a strong turf grass sod (although deeply and extensively rooted). The leaf blade vascular bundles of the Florida native seashore paspalum ecotypes are tough and fibrous and therefore do not exhibit good turf grass mowing characteristics, leaving protrusions of fibers extending from the cut edge of the leaf blade. The SGX-6 variety exhibits superior winter color retention compared to the Florida native seashore paspalum ecotypes. The Florida native seashore paspalum ecotypes do exhibit greater salinity tolerance than the SGX-6 variety, however. Table 1 below shows a comparison between the SGX-6 variety and native Florida varieties.

| | SGX-6 | FL Native |
|---|---|---|
| Leaf blade width | 1.4–1.9 mm | 3–8 mm |
| Leaf blade length | 1.75–2.25 cm | 3.5–15 cm |
| Culm height | 1.5–3 cm | 50–70 cm |
| Raceme | 2 - paired | 2 - paired often w/ 1–2 |

-continued

| | SGX-6 | FL Native |
|---|---|---|
| branches | | digitate |
| Raceme length | 0.8–2.25 cm | 4–8 cm |
| Growth habit | Strong stoloniferous and Strong rhizomanous | Stoloniferous and Weakly rhizomanous |
| Turf density | Very High | Low |
| Sod strength | Very High | Low to Moderate |
| Mowing quality | Very Good | Moderate to Poor |
| Salinity tolerence | High (≧15,000 ppm TDS) | Very High (≧45,000 ppm TDS) |
| Winter Color | Excellent | Poor |

DNA Analysis

Comparative DNA amplification profiles of 'SGX-6', applicants' 'Seaway' seashore paspalum cultivar, 'Adalayd' grass, and a native seashore paspalum produced by the University of Tennessee Plant Molecular Genetics laboratory are shown in FIG. 3. "Ladder" denotes the molecular size markers in the left-most and right-most lanes, "214-1" is the 'Seaway' grass, "215-2" is the 'SGX-6' grass, "215-5" is the 'Adalayd' grass, and "215-6" is a native seashore paspalum. The profiles were generated using known DAF techniques with two different primers (8.6i and 10.6e) (see e.g., Caetano-Anolles, et al. *Bio/Technology* 9:553–557 (1991); U.S. Pat. No. 5,413,909; Bassam and Bentley, *Biotechniques* 19:568–573; U.S. Pat. No. 5,643,479). Based upon these results, it has been determined that the applicants' 'SGX-6' grass is genetically different from the native grass, the 'Adalayd' grass, as well as applicants' 'Seaway' cultivar.

We claim:

1. A new and distinct cultivar of seashore paspalum grass, substantially as herein illustrated and described, characterized by its fine texture when closely mown and its superior tolerance to salt, drought, and soil hypoxic conditions.

* * * * *